United States Patent [19]

Masuzawa et al.

[11] Patent Number: 4,894,458
[45] Date of Patent: Jan. 16, 1990

[54] QUINOLONECARBOXYLIC ACID DERIVATIVES AND THEIR PREPARATION

[75] Inventors: Kuniyoshi Masuzawa, Koga; Seigo Suzue; Keiji Hirai, both of Kuki; Takayoshi Ishizaki, Washimiya, all of Japan

[73] Assignee: Kyorin Pharmaceutical Co., Ltd., Tokyo, Japan

[21] Appl. No.: 233,363

[22] Filed: Aug. 18, 1988

Related U.S. Application Data

[63] Continuation-in-part of Ser. No. 26,194, Mar. 16, 1987, abandoned.

[30] Foreign Application Priority Data

Mar. 17, 1986 [JP] Japan .................................. 61-59016

[51] Int. Cl.$^4$ .......................................... C07D 401/04
[52] U.S. Cl. ....................................... 546/156; 540/575; 544/58.6; 544/128; 544/363
[58] Field of Search .......................................... 546/156

[56] References Cited

U.S. PATENT DOCUMENTS

| 4,473,568 | 9/1984 | Hutt | 544/363 |
| 4,499,091 | 2/1985 | Wentland et al. | 544/363 |
| 4,556,658 | 12/1985 | Grohe et al. | 544/363 |

FOREIGN PATENT DOCUMENTS

| 1141383 | 2/1983 | Canada | 544/363 |
| 60-126271 | 7/1985 | Japan | 544/363 |
| 2057440 | 4/1981 | United Kingdom | 544/363 |

Primary Examiner—Glennon H. Hollrah
Assistant Examiner—James H. Turnipseed
Attorney, Agent, or Firm—Oblon, Spivak, McClelland, Maier & Neustadt

[57] ABSTRACT

Quinolonecarboxylic acid derivatives of the following formula,

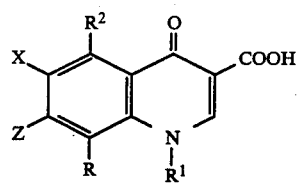

wherein R indicates straight or branched lower alkyl, $R^1$ indicates cycloalkyl having 3 to 6 carbon atoms, straight or branched lower alkyl, halogenoalkyl, alkenyl, hydroxyalkyl, lower alkylamino or substituted or non-substituted phenyl, $R^2$ indicates hydrogen, halogen, nitro or amino, X indicates halogen, Z indicates halogen, azetidino, pyrrolidino, piperidino, morpholino, thiomorpholino, piperazino or homopiperazino of the following formula,

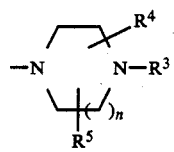

(here, n is 1 or 2, $R^3$ indicates hydrogen, lower alkyl, lower acyl, acyloxycarbonyl or benzyl, $R^4$ and $R^5$ indicate hydrogen, lower alkyl, aminoalkyl, hydroxyalkyl or phenyl each independently), or pyrrolidino or piperidino of the following formula,

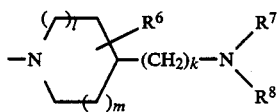

(here, k is 0, 1 or 2, l is 0, 1 or 2, m is 0 or 1, $R^6$ indicates hydrogen, lower alkyl or hydroxy, $R^7$ indicates hydrogen, lower alkyl, halogenoalkyl or hydroxyalkyl, $R^8$ indicates hydrogen, lower alkyl, lower acyl, alkoxycarbonyl or benzyl), the hydrates and pharmaceutically acceptable acid addition or alkali salts thereof are useful as antibacterial agents.

8 Claims, No Drawings

QUINOLONECARBOXYLIC ACID DERIVATIVES AND THEIR PREPARATION

DETAILED DESCRIPTION OF THE INVENTION

The present invention relates to novel quinolonecarboxylic acid derivatives having excellent properties as antibacterial agent, process for their preparation, and antibacterial agents containing these novel compounds.

Compounds of this invention are characterized in having an alkyl group at 8-position of the quinolonecarboxylic acid.

Since nalidixic acid which has been employed for treatment of urinary tract infections by gram-negative bacteria, was introduced in 1963, intensive work has been carried out on the further development of quinolonecarboxylic acid analogue.

Recently, norfloxacin, which has been developed by us, shows high antibacterial activity against gram-negative bacteria including Pseudomonas aeruginosa and gram-positive bacteria. This compound is widely used clinically as new quinolonecarboxylic acid-antibacterial agent having a broad antibacterial spectrum. Afterwards, efforts are focusing on improvement of bioavailability of norfloxacin or strengthing its antibacterial activity.

Consequently, quinolonecarboxylic acid derivatives, having similar substituents, such as ofloxacin and ciprofloxacin have been developed.

Ciprofloxacin has stronger antibacterial activity than norfloxacin. However, the antibacterial potency against gram-positive bacteria is considerably inferior to that against gram-negative bacteria. Furthermore, when administered orally to animals or human being, such high effect as expected from in vitro activity thereof cannot be obtained. Therefore, it is said that it has a difficulty in the oral absorptivity or the bioavailability.

On the other hand, gram-positive bacteria including staphylococci such as methicillin- and cephalosporin-resistant Staphylococcus aureus, Staphylococcus epidermidis, etc., enterococci, hemolytic streptococci and others, which exhibit high resistance to β-lactam-based antibiotics, in particular, to third generation cephalosporin-based ones, have made a question again clinically.

In addition, it has become clear that the obligate anaerobes on skin or mucous membrane act as the pathogen of opportunistic infection in the light of the popularization of anaerobes inspection as a result of the development of clinical testing technology. It is reported that anaerobic bacteria are found with or without aerobic bacteria at a rate of 50 to 80% on respiratory organ infections, intraperitoneal infections, chronic otits media, paranasal sinusitis and infections even in the gyneclogical region. In such situation, the resistance of anaerobic bacteria having been sensible to the drugs such as clindamycin etc. hitherto has been increased and a serious problem is posed for the choice of chemotherapeutic agents.

As the result of the continuation of our tireless study thereafter, it was noticed that the substituent on 8-position played extremely important roles in the extension of antibacterial spectrum, the increase in activity and the oral absorption as a drug. Namely, various substituents were introduced to 8-position by us, and these compounds were analyzed using techniques such as quantitative structure activity relationship. We have reached to the conclusion that alkyl quite unexpectedly is optimal as the substituent at 8-position.

Based on these study, the inventors have found novel compounds of this invention exhibit extremely high activity against aerobic gram-negative including Pseudomonas aeruginosa and-positive bacteria, and besides anaerobic bacteria and Mycoplasma that show less susceptibility to conventional quinolonecarboxylic acids.

The present compounds are well absorbed and distributed into the tissue when administered orally in animals and thus constitute valuable agents for the treatment of infectious human or animal diseases.

The invention provides quinolonecarboxylic acid derivatives of the formula (I),

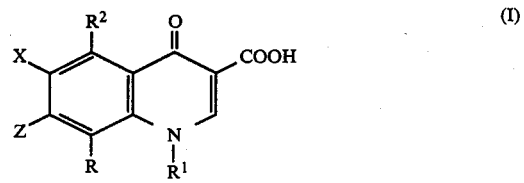

(I)

wherein R indicates straight or branched lower alkyl, $R^1$ indicates cycloalkyl having 3 to 6 carbon atoms, straight or branched lower alkyl, halogenoalkyl, alkenyl, hydroxyalkyl, lower alkylamino or substituted or non-substituted phenyl, $R^2$ indicates hydrogen, halogen, nitro or amino, X indicates halogen, Z indicates halogen, azetidino, pyrrolidino, piperidino, morpholino, thiomorpholino, piperazino or homopiperazino of the following formula,

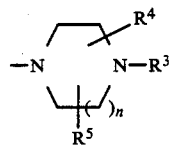

(here, n is 1 or 2, $R^3$ indicates hydrogen, lower alkyl, lower acyl, acyloxycarbonyl or benzyl, $R^4$ and $R^5$ indicate hydrogen, lower alkyl, aminoalkyl, hydroxyalkyl or phenyl each independently), or pyrrolidino or piperidino of the following formula,

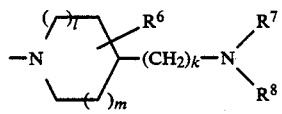

(here, k is 0, 1 or 2, l is 0, 1 or 2, m is 0 or 1, $R^6$ indicates hydrogen, lower alkyl or hydroxy, $R^7$ indicates hydrogen, lower alkyl, halogenoalkyl or hydroxyalkyl, $R^8$ indicates hydrogen, lower alkyl, lower acyl, alkoxycarbonyl or benzyl), the hydrates and pharmaceutically acceptable acid addition or alkali salts thereof.

In following, explanation is made about the preparation process for the compound of the invention.

Compound of the formula (IV);

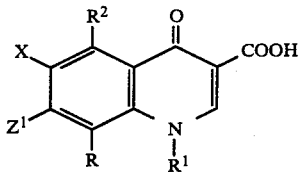

wherein R, R¹, R² and X have the above-stated meanings, and Z¹ indicates azetidino, pyrrolidino, piperidino, morpholino, thiomorpholino, piperazino or homopiperazino of the following formula,

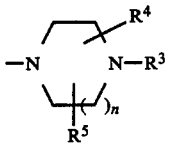

(here, n is 1 or 2, R³ indicates hydrogen, lower alkyl, lower acyl, acyloxycarbonyl or benzyl, R⁴ and R⁵ indicate hydrogen, lower alkyl, aminoalkyl, hydroxyalkyl or phenyl each independently), or pyrrolidino or piperidino of the following formula,

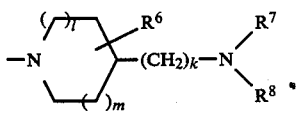

(here, k is 0, 1 or 2, l is 0, 1 or 2, m is 0 or 1, R⁶ indicates hydrogen, lower alkyl or hydroxy, R⁷ indicates hydrogen, lower alkyl, halogenoalkyl or hydroxyalkyl, R⁸ indicates hydrogen, lower alkyl, lower acyl, alkoxycarbonyl or benzyl) are prepared by allowing compound of the formula (II);

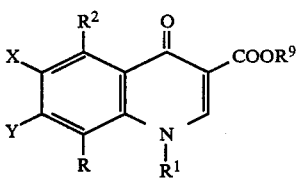

wherein Y indicates halogen, R⁹ indicates hydrogen or lower alkyl, and R, R¹, R² and X have the above-stated meanings, to condense with cyclic amines of the formula (III);

Z¹—H  (III)

wherein Z¹ has the above-stated meanings.

The reaction between the compound of the formula (II) and the compound of the formula (III) can be conducted in the absence of solvent or in the presence of polar solvents such as water, alcohols, acetonitrile, dimethylformamide (DMF), dimethyl sulfoxide (DMSO), hexamethylphosphoric amide (HMPA), pyridine, picoline etc. The reaction temperature is selected appropriately within a range of room temperature to 200° C., preferably room temperature to 160° C. In more detail, it is suitable to allow the compound of the formula (II) to react with 1 to 5 times mole of the compound of the formula (III) for 1 to 50 hours at room temperature to 120° C. in 2 to 10 times volume of the solvents.

At this time, the use of deacidifying agents such as triethylamine, diazabicyclo bases and potassium carbonate is also preferable.

Moreover, in the case of compound of the formula (I) in which R⁹ indicates lower alkyl, they are converted to quinolonecarboxylic acid derivatives of the formula (I');

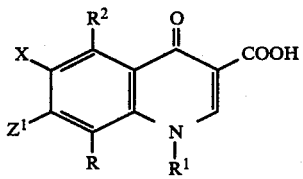

wherein R, R¹, R², X and Z¹ have the above-stated meanings, by hydrolysis according to usual method.

Such hydrolysis can be carried out easily at room temperature to boiling point of solvent in water, alcohols or mixed solutions thereof using alkalies such as sodium hydroxide and potassium hydroxide or acids such as hydrochloric acid and sulfuric acid.

The synthetic intermediates of the formula (II) for the preparation of the compounds of the invention are also novel compounds and can be prepared through, for example, following route.

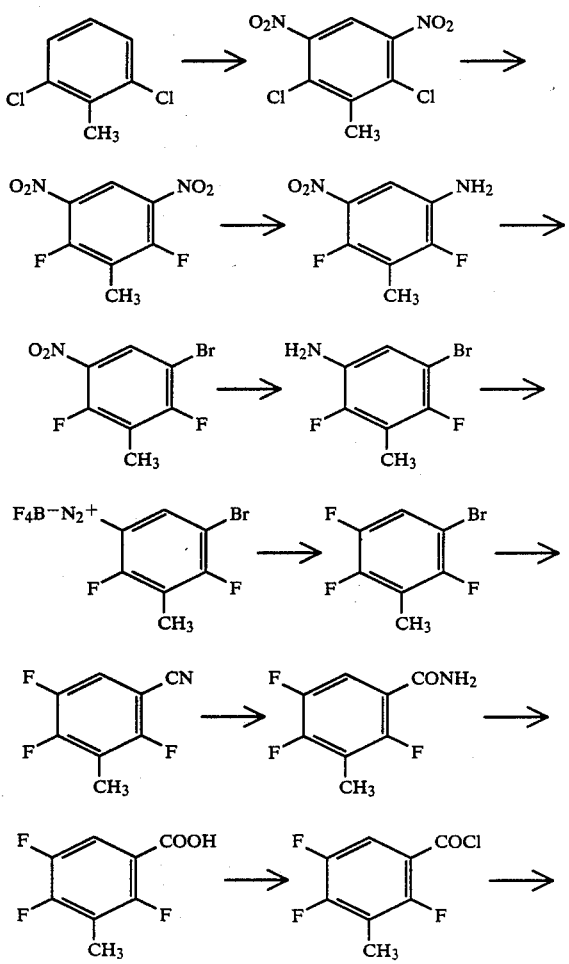

-continued

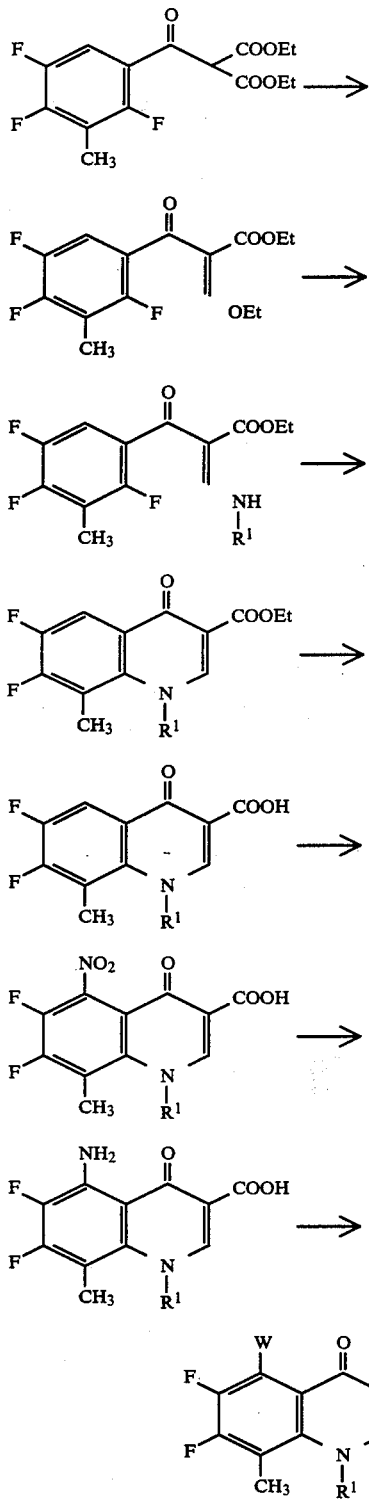

wherein W indicates halogen and R¹ has the above-stated meanings.

Next, the compound of the formula (I) can be converted to the salts thereof according to usual method, if necessary. As the salts, for example, those with inorganic acids such as hydrochloric acid, sulfuric acid, phosphoric acid, etc., those with organic acids such as methanesulfonic acid, lactic acid, oxalic acid, acetic acid, etc., or salts of sodium, potassium, magnesium, calcium, aluminum, cerium, chromium, cobalt, copper, iron, zinc, platinum, silver, etc. can be mentioned.

Furthermore, when the compounds of the invention are administered to human being or animals and plants, the shapes and the routes well known pharmaceutically up to this time are applied. They are used orally or parenterally through, for example, powders, tablets, capsules, ointments, injections, syrups, liquids, eye drops, suppositories, etc.

The following examples will further illustrate the invention without, however, limiting thereto.

EXAMPLE 1

2,6-Dichloro-3,5-dinitrotoluene

To the mixture of 2,6-dichlorotoluene (24.2 g) in concentrated sulfuric acid (100 ml) was added nitric acid fuming (d=1.52, 30 ml) dropwise during 20 minutes with stirring sufficiently. Further stirred at room temperature for an hour, the reacting mixture was poured into ice-water, the resulting precipitate was collected by filtration, washed with water sufficiently and recrystallized from EtOH (400 ml) to give the title compound (34.34 g) as pale green needles, mp 131°–132° C.

Analysis (%) for $C_7H_4Cl_2N_2O_4$, Calcd. (Found): C, 33.49 (33.49); H, 1.61 (1.52); N, 11.16 (10.95).

EXAMPLE 2

2,6-Difluoro-3,5-dinitrotoluene

To the suspension of potassium fluoride (4.7 g) in anhydrous DMSO (30 ml) was added 2,6-dichloro-3,5-dinitrotoluene (5.0 g) portionwise and stirred at 90° to 100° C. on an oil bath for 30 minutes. After cooling, the reacting mixture was poured into ice-water (100 ml) and benzene (50 ml), stirred sufficiently and filtered through the Celite pad. This Celite pad was washed with benzene, filtrate and washings were combined and washed with water successively. To the organic layer were added aqueous potassium carbonate solution and active carbon, stirred sufficiently and filtered off. The filtrate was separated, washed with water, dried over anhydrous sodium sulfate and then concentrated under reduced pressure. The resulting residue was recrystallized from ethanol to give the title compound (2.47 g) as pale yellow needles, mp 81°–82° C.

Analysis (%) for $C_7H_4F_2N_2O_4$, Calcd. (Found): C, 38.54 (38.54); H, 1.85 (1.80); N, 12.84 (12.70).

EXAMPLE 3

2,4-Difluoro-3-methyl-5-nitroaniline

To a suspension of iron powder (16.8 g, 100 mesh) in water (140 ml), with vigorous stirring at 50° C., was slowly added concentrated hydrochloric acid (3 ml). After hot ethanol (90 ml) was mixed, 2,6-difluoro-3,5-dinitrotoluene (21.8 g) was added portionwise to the suspension at 55° to 56° C. during 5 minutes. After stirring for 1.5 hours at 55° to 60° C., to the reacting mixture was added sodium hydrogensulfate (3.48 g) and stirred for further 30 minutes at the same temperature. To the reacting mixture was added benzene (100 ml), stirred for 10 minutes and insoluble materials were filtered off, and then the materials were washed with benzene. To the filtrate and washings were added water and active carbon, stirred sufficiently and filtered off.

The organic layer was separated and the water layer was further extracted with benzene. The organic layer was combined, washed with water, dried over anhydrous sodium sulfate and concentrated under reduced pressure to give the title compound (11.82 g) as pale brown crystals.

This crystals were recrystallized from aqueous ethanol to give yellowish brown prisms, mp 106°–107° C.

Analysis (%) for $C_7H_6F_2N_2O_2$, Calcd. (Found): C, 44.69 (44.74); H, 3.22 (3.16); N, 14.89 (14.98).

EXAMPLE 4

3-Bromo-2,6-difluoro-5-nitrotoluene

To a mixture of anhydrous cupric bromide (67.6 g) and t-butyl nitrite (37.5 g) in anhydrous acetonitrile (50 ml) with vigorous stirring was added the mixture of 2,4-difluoro-3-methyl-5-nitroaniline (45.65 g) in anhydrous acetonitrile (100 ml) at 60° to 65° C. during 20 minutes. After stirring for further 10 minutes, the reacting mixture was poured into aqueous hydrochloric acid solution (concentrated hydrochloric acid:water=2:1) and extracted with ether. The organic layer was washed with aqueous hydrochloric acid solution and water successively, dried over anhydrous sodium sulfate and concentrated under reduced pressure. The resulting residue was distilled under reduced pressure to give the title compound (32.86 g), bp 100°–117° C./15 mmHg.

EXAMPLE 5

5-Bromo-2,4-difluoro-3-methylaniline

To a suspension of iron powder (26.6 g, 100 mesh) in water (60 ml), with vigorous stirring at 50° C., was slowly added concentrated hydrochloric acid (4 ml). After hot ethanol (120 ml) was mixed, 3-bromo-2,6-difluoro-5-nitrotoluene (40 g) was added dropwise to the suspension at 75° to 78° C. during 30 minutes. The reacting mixture was refluxed for 1 hour, insoluble materials were filtered off through Celite pad, and then the materials were washed with hot ethanol. To the filtrate and washings were added ice water (400 ml) and the resulting precipitate was recrystallized from hexane to give the title compound (18.66 g) as pale brown needles, mp 68°–68.5° C.

Analysis (%) for $C_7H_8BrF_2N$, Calcd. (Found): C, 37.86 (37.23); H, 2.72 (2.62); N, 6.31 (6.16).

EXAMPLE 6

5-Bromo-2,4-difluoro-3-methylbenzenediazonium tetrafluoroborate

To a suspension of 5-bromo-2,4-difluoro-3-methylaniline (24.60 g) in 42% fluoroboric acid (150 ml) with stirring vigorously at −3° to 0° C. was added sodium nitrite (11.47 g) in water (20 ml) dropwise during 40 minutes. After stirring for 1.5 hours at 0° to 5° C., the reacting mixture was cooled with ice bath sufficiently and the resulting precipitate was collected by filtration. This precipitate was washed with small portion of water and ether and dried under reduced pressure to give the title compound (28.83 g) as pale brown prisms, mp 147°–150° C. (decompd.).

IR ($cm^{-1}$, KBr): 2300 (−N≡N+).

EXAMPLE 7

3-Bromo-2,5,6-trifluorotoluene

To the sea-sand (30 g; 50–80 mesh) in distillating flask was added 5-bromo-2,4-difluoro-3-methylbenznendiazonium tetrafluoroborate (30.0 g) and heated up with gas burner. After finishing the gas-flow, the flask and the vessel were washed with dichloromethane (50 ml). The organic layer was washed with water, dried over anhydrous sodium sulfate and concentrated under reduced pressure. The resulting residue was distilled under reduced pressure to give the title compound (11.83 g) as colorless oil, bp 88°–95° C./45 mmHg.

NMR ($\delta$ in $CDCl_3$): 2.27 (3H, t, J=2.2 Hz), 7.23 (1H, ddd).

EXAMPLE 8

2,4,5-Trifluoro-3-methylbenzonitrile

A mixture of 3-bromo-2,5,6-trifluorotoluene (11.0 g) and cupric cyanide (5.3 g) in N-methylpyrrolidone (15 ml) was stirred at 150° to 160° C. in a sealed tube for 4.5 hours. After cooling, to the reacting mixture was added a solution of ferric chloride (20 g) and concentrated hydrochloric acid (5 ml) in water (30 ml) and stirred at 50° to 60° C. for 20 minutes. The reacting mixture was extracted with ether, the organic layer was washed with aqueous hydrochloric acid solution, water and saturated aqueous sodium chloride solution successively, dried over anhydrous sodium sulfate and concentrated under reduced pressure to give the title compound (7.83 g) as pale brown oil.

IR ($cm^{-1}$, neat): 2260 (CN).

NMR ($\delta$ in $CDCl_3$): 2.30 (3H, dt, J=0.4, 2.2 Hz), 7.23 (1H, ddd).

EXAMPLE 9

2,4,5-Trifluoro-3-methylbenzamide

A mixture of 2,4,5-trifluoro-3-methylbenzonitrile (0.50 g) in concentrated sulfuric acid (0.3 ml) was stirred on an oil bath (90° to 100° C.) for 1 hour. After cooling, to the reacting mixture was added ice-water (5 ml), the resulting precipitate was collected by filtration, washed with water sufficiently and dried to give the title compound (0.52 g), mp 105°–108° C. This crystals were recrystallized from hexane to give colorless crystals, mp 112°–113° C.

Analysis (%) for $C_8H_6F_3NO$, Calcd. (Found): C, 50.80 (50.93); H, 3.20 (3.19); N, 7.41 (7.42).

EXAMPLE 10

2,4,5-Trifluoro-3-methylbenzoic acid (a) A mixture of 2,4,5-trifluoro-3-methylbenzamide (0.38 g) in 18N sulfuric acid (3 ml) was stirred on an oil bath (100° to 110° C.) for 2 hours. After cooling, to the reacting mixture was added ice-water (10 ml), the resulting precipitate was collected by filtration and recrystallized from hexane to give the title compound (0.30 g) as colorless needles, mp 103°–105° C.

Analysis (%) for $C_8H_5F_3O_2$, Calcd. (Found): C, 50.54 (50.97); H, 2.65 (2.72).

(b) A mixture of 2,4,5-trifluoro-3-methylbenzonitrile (7.17 g) in concentrated sulfuric acid (4.5 ml) was stirred on an oil bath (90° to 100° C.) for 1 hour. After cooling, to the reacting mixture were added ice-water (21 ml) and concentrated sulfuric acid (16.5 ml), further stirred on an oil bath (100° to 110° C.) for 3 hours. After cooling, to the reacting mixture was added ice-water (150 ml), the resulting precipitate was collected by filtration and the precipitate was dissolved in dichloromethane (60 ml). The organic layer was dried over anhydrous sodium sulfate, concentrated under reduced pressure and recrystallized from hexane to give the title compound (6.11 g) as colorless needles, mp 101°–102° C.

Analysis (%) for $C_8H_5F_3O_2$, Calcd. (Found): C, 50.54 (50.93); H, 2.65 (2.77).

EXAMPLE 11

2,4,5-Trifluoro-3-methylbenzoyl chloride

A mixture of 2,4,5-trifluoro-3-methylbenzoic acid (6.0 g), thionyl chloride (26 ml) and DMF (0.01 ml) was refluxed for 4 hours. Then excess thionyl chloride was removed under reduced pressure, the resulting residue was distilled under reduced pressure to give the title compound (4.51 g) as pale yellow liquid, bp 90°–92° C./40 mmHg.

NMR ($\delta$ in $CDCl_3$): 1.58–2.32 (3H, m), 7.67–7.95 (1H, m).

EXAMPLE 12

Diethyl 2-(2,4,5-trifluoro-3-methylbenzoyl)malonate

To a mixture of magnesium turnings (0.69 g) and absolute ethanol (4.7 ml) was added carbon tetrachloride (0.4 ml). To the stirring suspension was added a solution of diethyl malonate (4.41 g) and absolute ethanol (4.7 ml) in anhydrous toluene (19.2 ml) dropwise during 10 minutes at 15° to 50° C. After the mixture was stirred at 50° to 60° C. for 2 hours, to the mixture was added a solution of 2,4,5-trifluoro-3-methylbenzoyl chloride (4.51 g) in anhydrous toluene (6.4 ml) dropwise at $-16°$ to $-13°$ C. during 10 minutes. The reacting mixture was stirred at $-20°$ C. for 1 hour, and then warmed gradually to room temperature during 1.5 hours with stirring. To this solution was added ice water (25 ml) containing concentrated sulfuric acid (0.8 ml), extracted with toluene. The organic layer was washed with saturated aqueous sodium chloride solution, dried over anhydrous sodium chloride and concentrated under reduced pressure to give the title compound (8.10 g).

IR ($cm^{-1}$, neat): 1760–1740

1690 (C=O).

EXAMPLE 13

Ethyl 2-(2,4,5-trifluoro-3-methylbenzoyl)acetate

A mixture of diethyl 2-(2,4,5-trifluoro-3-methylbenzoyl)malonate (8.10 g) and p-toluenesulfonic acid (9.6 mg) in water (9.6 ml) was refluxed for 3 hours with stirring vigorously. After cooling, the reacting mixture was extracted with dichloromethane. The organic layer was washed with 7% aqueous sodium bicarbonate solution, dried over anhydrous sodium sulfate and then concentrated under reduced pressure. The resulting residue was allowed to stand in a refrigerator for 2 days, the resulting precipitate was collected by filtration and recrystallized from n-hexane to give the title compound (0.51 g) as colorless prisms, mp 38°–39° C.

The washings were added to the mixture of p-toluenesulfonic acid (9.6 mg) in water (9.6 ml), then refluxed for 3 hours with stirring vigorously and treated with same manner to give the title compound (5.02 g) as yellow oil, further.

Analysis (%) for $C_{12}H_{11}F_3O_3$, Calcd. (Found): C, 55.39 (55.24); H, 4.26 (4.00).

EXAMPLE 14

Ethyl 2-(2,4,5-trifluoro-3-methylbenzoyl)-3-ethoxyacrylate

A mixture of ethyl 2-(2,4,5-trifluoro-3-methylbenzoyl)acetate (5.02 g), ethyl orthoformate (4.29 g) and acetic anhydride (4.93 g) was stirred at 130° to 135° C. for 5 hours and then concentrated under reduced pressure to give the title compound (6.05 g) as red oil.

IR ($cm^{-1}$, neat): 1720

1620 (C=O).

EXAMPLE 15

Ethyl 2-(2,4,5-trifluoro-3-methylbenzoyl)-3-cyclopropylaminoacrylate

To a solution of ethyl 2-(2,4,5-trifluoro-3-methylbenzoyl)ethoxyacrylate (6.05 g) in absolute ethanol (15 ml) was added a solution of cyclopropylamine (1.19 g) in absolute ethanol (9 ml) dropwise at 5° to 10° C. during 10 minutes with stirring. After stirring for 30 minutes at below 5° C., the mixture was concentrated under reduced pressure. To the resulting residue was added ether-n-hexane and the resulting precipitate was collected by filtration to give the title compound (1.78 g) as white powder, mp 73°–75° C.

The washings were purified by silica gel chromatography eluting with n-hexane-ethyl acetate (4:1) to give the title compound (1.22 g), further.

Analysis (%) for $C_{16}H_{16}F_3NO_3$, Calcd. (Found): C, 58.71 (59.00); H, 4.93 (4.90); N, 4.28 (4.25).

EXAMPLE 16

Ethyl 1-cyclopropyl-6,7-difluoro-1,4-dihydro-8-methyl-4-oxo-3-quinolinecarboxylate (a) A mixture of ethyl 2-(2,4,5-trifluoro-3-methylbenzoyl)-3-cyclopropylaminoacrylate (300 mg) and sodium fluoride (70 mg) in anhydrous DMF (2 ml) was stirred at 130° to 140° C. for 6 hours. To the reacting mixture was added ice-water (3 ml), the resulting precipitate was collected by filtration, washed with water and recrystallized from methanol to give the title compound (220 mg) as white needles, mp 220°–221° C.

Analysis (%) for $C_{16}H_{15}F_2NO_3$, Calcd. (Found): C, 62.54 (62.70); H, 4.92 (4.95); N, 4.56 (4.54).

(b) To the cooled mixture of 55% sodium hydride (50 mg) in anhydrous dioxane (2 ml) was added ethyl 2-(2,4,5-trifluoro-3-methylbenzoyl)-3-cyclopropylaminoacrylate (300 mg) slowly with stirring. After stirring for 30 minutes at room temperature, to the reacting mixture was added water (5 ml), the resulting precipitate was collected by filtration, washed with water and recrystallized from methanol to give the title compound (220 mg) as white needles.

EXAMPLE 17

1-Cyclopropyl-6,7-difluoro-1,4-dihydro-8-methyl-4-oxo-3-quinolinecarboxylic acid A mixture of ethyl 1-cyclopropyl-6,7-difluoro-1,4-dihydro-8-methyl-4-oxo-3-quinolinecarboxylate (1.97 g), concentrated sulfuric acid (1.6 ml) and acetic acid (12.8 ml) in water (9.6 ml) was refluxed for 1.5 hours. The reacting mixture was poured into ice-water (100 ml), the resulting precipitate was collected by filtration, washed with water and dried to give the title compound (1.58 g) as white powder, mp 243°–245° C.

Analysis (%) for $C_{14}H_{11}F_2NO_3$, Calcd. (Found): C, 60.23 (60.37); H, 3.97 (4.14); N, 5.02 (4.96).

EXAMPLE 18

7-(3-Amino-1-pyrrolidinyl)-1-cyclopropyl-6-fluoro-1,4-dihydro-8-methyl-4-oxo-3-quinolinecarboxylic acid A mixture of 1-cyclopropyl-6,7-difluoro-1,4-dihydro-8-methyl-4-oxo-3-quinolinecarboxylic acid (200 mg), 3-t-butoxycarbonylaminopyrrolidine (200 mg), 1,8-diazabicyclo[5,4,0]-7-undecene (110 mg, DBU) and anhydrous acetonitrile (2 ml) was refluxed for 18 hours. The reacting mixture was concentrated under reduced pressure. The resulting residue was dissolved in chloroform (20 ml), washed with 10% aqueous citric acid solution and saturated aqueous sodium chloride solution successively, dried over anhydrous sodium sulfate and concentrated under reduced pressure. To the solution of the resulting residue in methanol (2 ml) was added concentrated hydrochloric acid (2 ml) and stirred at room temperature for 15 minutes. After the reacting mixture was neutralized with concentrated aqueous ammonia, the mixture was concentrated under reduced pressure. The resulting residue was purified by silica gel chromatography eluting chloroform-methanol-concentrated aqueous ammonia (10:10:3) and recrystallized from dichloromethane-methanol further to give the title compound (30 mg) as yellow powder, mp 187°–190° C.

Analysis (%) for $C_{18}H_{20}FN_3O_3 \cdot 2\ H_2O$, Calcd. (Found): C, 56.68 (56.84); H, 6.34 (5.87); N, 11.02 (10.94).

Mass m/e=345 (M+).

IR (cm$^{-1}$, KBr): 1700

1630 (C=O).

NMR (δ in D$_2$O-NaOD): 0.60–1.30

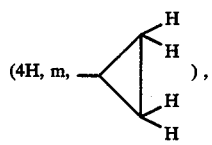

1.60–2.32

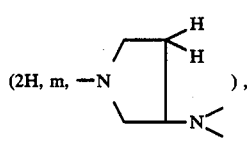

2.48 (3H, s, —CH$_3$), 3.00–3.80

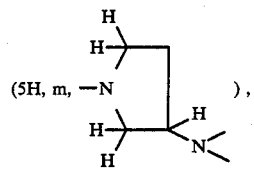

3.92–4.24

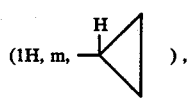

7.55 (1H, d, J=14.5 Hz, 5-H), 8.53 (1H, s, 2-H).

EXAMPLE 19

1-Cyclopropyl-6-fluoro-1,4-dihydro-8-methyl-4-oxo-7-(1-piperazinyl)-3-quinolinecarboxylic acid A mixture of 1-cyclopropyl-6,7-difluoro-1,4-dihydro-8-methyl-4-oxo-3-quinolinecarboxylic acid (200 mg), piperazine (250 mg) in anhydrous DMSO (2 ml) was stirred at 70° to 80° C. for 4 hours. After the reacting mixture was concentrated under reduced pressure, to the resulting residue was added methanol and the resulting precipitate was filtered off. After the filtrate was concentrated under reduced pressure, the resulting residue was purified by silica gel column chromatography eluting chloroform-methanol (20:1) chloroform-methanol-concentrated aqueous ammonia (10:10:1) and further purified by preparative thin layer chromatography eluting chloroform-methanol (20:1)→chloroform methanol-concentrated aqueous ammonia (10:10:1→10:10:3) to give the title compound (46 mg) as redish powder, mp 300° C.

Analysis (%) for $C_{18}H_{20}FN_3O_3 \cdot 9/4\ H_2O$, Calcd. (Found): C, 56.02 (56.87); H, 6.40 (5.88); N, 10.89 (11.09).

Mass m/e: 345 (M+).

NMR (δ in D$_2$O-NaOD): 0.70–1.34

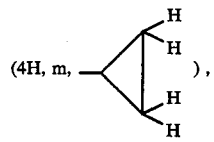

2.72 (3H, s, CH$_3$), 2.80–3.34

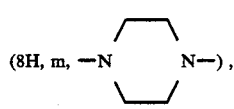

4.00–4.24

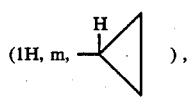

7.72 (1H, d, J=13.2 Hz, 5-H), 8.59 (1H, s, 2-H).

EXAMPLE 20

Ethyl 2-(2,4,5-trifluoro-3-methylbenzoyl)-3-ethoxyacrylate

A mixture of ethyl 2-(2,4,5-trifluoro-3-methylbenzoyl)acetate (3.0 g), ethyl orthoformate (2.6 g) and acetic anhydride (2.9 g) was stirred at 87° to 93° C. for 6 hours and then concentrated under reduced pressure to give the title compound (3.65 g) as orange oil.

EXAMPLE 21

Ethyl 2-(2,4,5-trifluoro-3-methylbenzoyl)-3-ethylaminoacrylate

To a solution of ethyl 2-(2,4,5-trifluoro-3-methylbenzoyl)ethoxyacrylate (3.65 g) in absolute ethanol (15 ml) was added a solution of ethylamine (0.82 g; 70% aqueous solution) in absolute ethanol (5 ml) dropwise at 5° to 10° C. during 15 minutes with stirring. After stirring for 35 minutes at the same temperature, the mixture was concentrated under reduced pressure. To the resulting residue was purified by silica gel chromatography eluting by n-hexane-ethyl acetate (4:1) and recrystallized from dichloromethane-n-hexane to give the title compound (2.66 g) as white powder, mp 110°-110.5° C.

Analysis (%) for $C_{15}H_{16}F_3NO_3$, Calcd. (Found): C, 57.14 (57.39); H, 5.11 (5.04); N, 4.44 (4.50).

EXAMPLE 22

Ethyl 1-ethyl-6,7-difluoro-1,4-dihydro-8-methyl-4-oxo-3-quinolinecarboxylate To the cooled mixture of 55% sodium hydride (0.47 g) in anhydrous dioxane (20 ml) was added ethyl 2-(2,4,5-trifluoro-3-methylbenzoyl)-3-ethylaminoacrylate (2.6 g) during 10 minutes with stirring. After stirring for 40 minutes at room temperature, the reacting mixture was poured into ice-water (50 ml), the resulting precipitate was collected by filtration, washed with chilled water and ether successively and recrystallized from dichloromethane-n-hexane to give the title compound (1.6 g) as colorless prisms, mp 177°-179.5° C.

Analysis (%) for $C_{15}H_{15}F_2NO_3$, Calcd. (Found): C, 61.01 (61.26); H, 5.12 (5.13); N, 4.74 (4.85).

EXAMPLE 23

1-Ethyl-6,7-difluoro-1,4-dihydro-8-methyl-4-oxo-3-quinolinecarboxylic acid

A mixture of ethyl 1-ethyl-6,7-difluoro-1,4-dihydro-8-methyl-4-oxo-3-quinolinecarboxylate (0.96 g), concentrated sulfuric acid (0.5 ml) and acetic acid (4 ml) in water (4 ml) was stirred for 70 minutes on an oil bath at 100° C. The reacting mixture was poured into ice-water (25 ml), the resulting precipitate was collected by filtration, washed with water sufficiently to give the title compound (0.8 g) as colorless flakes, mp 219°-221° C.

Analysis (%) for $C_{13}H_{11}F_2NO_3$, Calcd. (Found): C, 58.43 (58.44); H, 4.15 (4.15); N, 5.24 (5.27).

EXAMPLE 24

1-Ethyl-6-fluoro-1,4-dihydro-8-methyl-4-oxo-7-(1-piperazinyl)-3-quinolinecarboxylic acid A mixture of 1-ethyl-6,7-difluoro-1,4-dihydro-8-methyl-4-oxo-3-quinolinecarboxylic acid (350 mg), anhydrous piperazine (450 mg) in anhydrous DMSO (4 ml) was stirred at 50° to 72° C. for 18 hours. After the reacting mixture was concentrated under reduced pressure, the resulting residue was purified by silica gel column chromatography eluting chloroform-methanol-concentrated aqueous ammonia (20:6:1) to give the title compound (50 mg) as pale yellow flakes, mp 153°-156° C.

Analysis (%) for $C_{17}H_{20}FN_3O_3.9/5\ H_2O$, Calcd. (Found): C, 55.82 (55.79); H, 6.50 (6.54); N, 11.49 (11.29).

EXAMPLE 25

7-(3-Amino-1-pyrrolidinyl)-1-ethyl-6-fluoro-1,4-dihydro-8-methyl-4-oxo-3-quinolinecarboxylic acid A mixture of 1-ethyl-6,7-difluoro-1,4-dihydro-8-methyl-4-oxo-3-quinolinecarboxylic acid (420 mg), 3-t-butoxycarbonylaminopyrrolidine (350 mg), DBU (260 mg) and anhydrous acetonitrile (10 ml) was refluxed for 35 hours. After the reacting mixture was concentrated under reduced pressure, the resulting residue was dissolved in chloroform (40 ml), washed with 10% aqueous citric acid solution and saturated aqueous sodium chloride solution successively, dried over anhydrous sodium sulfate and concentrated under reduced pressure. The resulting residue was purified by silica gel column chromatography eluting chloroform-methanol-concentrated aqueous ammonia (20:6:1) and recrystallized from methanol to give 7-(3-t-butoxycarbonylamino-1-pyrrolidinyl)-1-ethyl-6-fluoro-1,4-dihydro-8-methyl-4-oxo-3-quinolinecarboxylic acid (360 mg) as white prisms, mp 184.5°-187.5° C. (decompd.).

Analysis (%) for $C_{22}H_{28}FN_3O_5.\frac{1}{2}\ H_2O$, Calcd. (Found): C, 59.72 (60.05); H, 6.61 (6.50); N, 9.50 (9.64).

This intermediate was added to the mixture of dichloromethane-trifluoroacetic acid (6 ml; 1:1 v/v), stirred for 9 hours at room temperature and then concentrated under reduced pressure. The resulting residue was purified by silica gel column chromatography eluting by chloroform-methanol-concentrated aqueous ammonia (20:6:1), to the resulting oil was added water and allowed to stand in a refrigerator. The resulting precipitate was collected by filtration and washed with chilled water sufficiently to give the title compound (15 mg) as pale green prisms, mp 187°-194.5° C. (decompd.).

Analysis (%) for $C_{17}H_{20}FN_3O_3.H_2O$, Calcd. (Found): C, 58.11 (58.44); H, 6.31 (6.49); N, 11.96 (11.91).

Experiment 1

Antibacterial spectrum

Minimal inhibitory concentrations (MICs) were determined in accordance with the method recommended by Japan Society of Chemotherapy. The results are shown in Table 1.

TABLE 1-a

| | In vitro antibacterial activity (aerobic bacteria) | | | | |
|---|---|---|---|---|---|
| | | MIC (μg/ml) | | | |
| Organism ($10^6$ cells/ml) | Gram | Exp. 18 | Exp. 19 | Exp. 25 | CPFX |
| *Bacillus subtilis* PCI 219 | + | 0.025 | 0.05 | 0.10 | 0.05 |

TABLE 1-a-continued

In vitro antibacterial activity (aerobic bacteria)

| Organism ($10^6$ cells/ml) | Gram | Exp. 18 | Exp. 19 | Exp. 25 | CPFX |
|---|---|---|---|---|---|
| *Staphylococcus aureus* 209 P | + | 0.05 | 0.20 | 0.20 | 0.20 |
| *S. aureus* IID 670 (Terajima) | + | 0.05 | 0.20 | 0.20 | 0.20 |
| *S. epidermidis* IID 866 | + | 0.05 | 0.20 | 0.20 | 0.20 |
| *Escherichia coli* NIHJ JC-2 | − | ≦0.0032 | 0.125 | 0.0125 | ≦0.0063 |
| *E. coli* ATCC 10536 | − | 0.0125 | 0.05 | 0.025 | 0.0125 |
| *Proteus vulgaris* IFO 3167 | − | 0.0125 | 0.025 | 0.0125 | 0.0125 |
| *P. mirabilis* IID 994 | − | 0.0125 | 0.025 | 0.05 | 0.025 |
| *Morganella morganii* IID 602 | − | 0.05 | 0.10 | 0.20 | 0.05 |
| *Klebsiella pneumoniae* KY(GN)6445 | − | 0.025 | 0.05 | 0.10 | 0.0125 |
| *K. pneumoniae* 1-220S | − | 0.05 | 0.05 | 0.10 | 0.05 |
| *Enterobacter cloacae* IID 977 | − | 0.025 | 0.05 | 0.10 | 0.025 |
| *Citrobacter freundii* IID 976 | − | 0.025 | 0.05 | 0.05 | 0.0125 |
| *Serratia marcescens* IID 618 | − | 0.05 | 0.05 | 0.05 | 0.05 |
| *Shigella sonnei* IID 969 | − | 0.0125 | 0.025 | 0.05 | 0.0125 |
| *Salmonella enteritidis* IID 604 | − | 0.025 | 0.05 | 0.05 | 0.0125 |
| *Pseudomonas aeruginosa* V-1 | − | 0.05 | 0.10 | 0.39 | 0.05 |
| *P. aeruginosa* IFO 12689 | − | 0.20 | 0.78 | 1.56 | 0.20 |
| *P. aeruginosa* IID 1210 | − | 0.20 | 0.78 | 0.78 | 0.39 |
| *P. cepacia* GIFU 518 | − | 0.20 | 0.78 | 1.56 | 0.39 |
| *P. maltophilia* GIFU 2491 | − | 0.10 | 0.39 | 1.56 | 0.39 |
| *Yersinia enterocolitica* IID 981 | − | 0.05 | 0.05 | 0.10 | 0.05 |
| *Acinetobacter anitratus* IID 876 | − | 0.05 | 0.20 | 0.78 | 0.10 |
| *Alcaligenes faecalis* 0114002 | − | 0.10 | 0.39 | 0.78 | 0.20 |

TABLE 1-b

In vitro antibacterial activity (anaerobic bacteria)

| Organism ($10^6$ cells/ml) | Gram | Exp. 18 | Exp. 19 | Exp. 25 | CPFX |
|---|---|---|---|---|---|
| *Bacteroides fragilis* GM 7000 | − | 0.20 | 0.78 | 3.13 | 6.25 |
| *B. fragilis* 0558 | − | 0.10 | 0.39 | 1.56 | 3.13 |
| *B. fragilis* 25285 | − | 0.20 | 0.78 | 1.56 | 3.13 |
| *B. distasonis* 8503 | − | 0.39 | 1.56 | 6.25 | 3.13 |
| *B. thetaiotaomicron* (0661) | − | 0.78 | 6.25 | 6.25 | 12.5 |
| *Fusobacterium necrophorum* S-45 | − | 0.10 | 0.39 | 1.56 | 0.78 |
| *F. varium* KYA 8501 | − | 0.78 | 3.13 | 6.25 | 12.5 |
| *Eubacterium lentum* GAI 5242 | + | 0.20 | 0.20 | 0.78 | 0.78 |
| *Propionibacterium acens* 11828 | + | 0.78 | 6.25 | 12.5 | 12.5 |
| *Peptococcus magnus* KY 017 | + | 0.05 | 0.39 | 0.39 | 0.39 |
| *Clostridium difficile* I-E | + | 0.78 | 3.13 | 6.25 | 12.5 |
| *C. perfringens* KYA 13123 | + | 0.05 | 0.20 | 0.78 | 0.39 |
| *C. ramosum* | + | 1.56 | 6.25 | 12.5 | 12.5 |
| *Peptostreptococcus anaerobius* KYA 27337 | + | 0.10 | 0.78 | 1.56 | 1.56 |
| *Pst micros* UPI 5464-1 | + | 0.10 | 0.39 | 0.39 | 0.20 |
| *Veillonella parvula* KYA 10790 | − | 0.10 | 0.39 | 0.39 | 0.20 |

CPFX: ciprofloxacin

EXAMPLE 26

7-(3,4-trans-3-t-Butoxycarbonylamino-4-methyl-1-pyrrolidinyl)-1-cyclopropyl-6-fluoro-1,4-dihydro-8-methyl-4-oxo-3-quinolinecarboxylic acid A mixture of 1-cyclopropyl-6,7-difluoro-1,4-dihydro-8-methyl-4-oxo-3-quinolinecarboxylic acid (0.50 g), 3-t-butoxycarbonylamino-4-methylpyrrolidine (0.54 g) and DBU (0.41 g) in anhydrous acetonitrile (5 ml) was refluxed for 20 hours with stirring under an atmosphere of argon. After the reacting mixture was concentrated under reduced pressure, the resulting residue was dissolved in dichloromethane (20 ml), washed with 10% aqueous citric acid solution, water and saturated aqueous sodium chloride solution successively, dried over anhydrous sodium sulfate and concentrated under reduced pressure. The resulting residue was purified by silica gel column chromatography eluting chloroform-→acetonitrile-dichloromethane and recrystallized from ethanol to give the title compound (0.34 g) as pale green prisms, mp 206°–209° C.

Analysis (%) for $C_{24}H_{30}FN_3O_5 \cdot H_2O$, Calcd. (Found): C, 60.36 (60.56): H. 6.75 (6.34); N, 8.80 (8.81).

EXAMPLE 27

7-(3,4-trans-3-Amino-4-methyl-1-pyrrolidinyl)-1-cyclopropyl-6-fluoro-1,4-dihydro-8-methyl-4-oxo-3-quinolinecarboxylic acid To the mixture of 7-(3,4-trans-3-t-butoxycarbonylamino-4-methyl-1-pyrrolidinyl)-1-cyclopropyl-6-fluoro-1,4-dihydro-8-methyl-4-oxo-3-quinolinecarboxylic acid (270 mg) in dichloromethane (5 ml) was added trifluoroacetic acid (5 ml) portionwise at room temperature and the reacting mixture was stirring at the same temperature for 30 minutes. After the reacting mixture was concentrated under reduced pressure, the resulting residue was dissolved in water (5 ml) and neutralized with aqueous sodium hydroxide solution. The resulting precipitate was collected by filtration to give the title compound (183 mg) as pale yellow needles, mp 177°–179° C.

Analysis (%) for $C_{19}H_{22}FN_3O_3$, Calcd. (Found): C, 63.50 (63.27); H, 6.17 (6.14); N, 11.69 (11.62).

EXAMPLE 28

7-(3,4-cis-3-Amino-4-methyl-1-pyrrolidinyl)-1-cyclopropyl-6-fluoro-1,4-dihydro-8-methyl-4-oxo-3-quinolinecarboxylic acid A mixture of 1-cyclopropyl-6,7-difluoro-1,4-dihydro-8-methyl-4-oxo-3-quinolinecarboxylic acid (0.50 g), 3,4-cis-3-t-butoxycarbonylamino-4-methylpyrrolidine (0.54 g) and DBU (0.41 g) in anhydrous acetonitrile (5 ml) was refluxed for 20 hours with stirring under an atmosphere of argon. After the reacting mixture was concentrated under reduced pressure, the resulting residue was dissolved in dichloromethane (20 ml), washed with 10% aqueous citric acid solution, water and saturated aqueous sodium chloride solution successively, dried over anhydrous sodium sulfate and concentrated under reduced pressure to give yellowish brown oil. To the mixture of this oil in dichloromethane (10 ml) was added trifluoroacetic acid (10 ml) portionwise and stirred for 30 minutes at room temperature. After the reacting mixture was concentrated under reduced pressure, the resulting residue was dissolved in diluted hydrochloric acid solution (water 40 ml-concentrated hydrochloric acid (0.5 ml), washed with dichloromethane, then the water layer was neutralized with aqueous sodium hydroxide solution and concentrated under reduced pressure. The resulting residue was purified by silica gel column chromatography eluting chloroform-methanol-concentrated aqueous ammonia (10:10:3), further MIC gel CHP20P column eluting water→water-methanol and recrystallized from methanol to give the title compound (82 mg) as pale brownish prisms, mp 222°–224° C.

Analysis (%) for $C_{19}H_{22}FN_3O_3 \cdot \frac{1}{2} H_2O$, Calcd. (Found): C, 61.94 (62.04); H, 6.29 (6.07); N, 11.41 (11.39).

TABLE 1-c

| | | MIC (μg/ml) | | |
|---|---|---|---|---|
| Organism ($10^6$ cells/ml) | Gram | Ex. 27 | Ex. 28 | CPFX |
| In vitro antibacterial activity (aerobic bacteria) | | | | |
| Bacillus subtilis PCI 219 | + | 0.0125 | 0.0125 | 0.05 |
| Staphylococcus aureus 209 P | + | 0.025 | 0.025 | 0.20 |
| S. aureus IID 670 (Terajima) | + | 0.025 | 0.025 | 0.20 |
| S. epidermidis IID 866 | + | 0.05 | 0.05 | 0.20 |
| Escherichia coli NIHJ JC-2 | − | 0.0063 | 0.0063 | 0.0063 |
| E. coli ATCC 10536 | − | 0.0063 | 0.0063 | 0.0125 |
| Proteus vulgaris IFO 3167 | − | 0.0063 | 0.0063 | 0.0125 |
| P. mirabilis IID 994 | − | 0.025 | 0.025 | 0.0125 |
| Morganella morganii IID 602 | − | 0.05 | 0.025 | 0.025 |
| Klebsiella pneumoniae KY(GN)6445 | − | 0.0125 | 0.0125 | 0.0125 |
| K. pneumoniae 1-220S | − | 0.025 | 0.05 | 0.05 |
| Enterobacter cloacae IID 977 | − | 0.025 | 0.025 | 0.025 |
| Citrobacter freundii IID 976 | − | 0.0063 | 0.0125 | 0.0063 |
| Serratia marcescens IID 618 | − | 0.05 | 0.05 | 0.05 |
| Shigella sonnei IID 969 | − | 0.0063 | 0.0063 | 0.0125 |
| Salmonella enteritidis IID 604 | − | 0.025 | 0.025 | 0.0125 |
| Pseudomonas aeruginosa V-1 | − | 0.20 | 0.10 | 0.10 |
| P. aeruginosa IFO 12689 | − | 0.39 | 0.39 | 0.20 |
| P. aeruginosa IID 1210 | − | 0.39 | 0.39 | 0.78 |
| P. cepacia GIFU 518 | − | 0.20 | 0.39 | 0.78 |
| P. maltophilia GIFU 2491 | − | 0.05 | 0.10 | 0.39 |
| Yersinia enterocolitica IID 981 | − | 0.025 | 0.0125 | 0.05 |
| Acinetobacter anitratus IID 876 | − | 0.025 | 0.05 | 0.20 |
| Alcaligenes faecalis 0114002 | − | 0.10 | 0.10 | 0.39 |

TABLE 1-d

| | | MIC (μg/ml) | | |
|---|---|---|---|---|
| Organism ($10^6$ cells/ml) | Gram | Ex. 27 | Ex. 28 | CPFX |
| In vitro antibacterial activity (anaerobic bacteria) | | | | |
| Bacteroides fragilis GM 7000 | − | 0.10 | 0.20 | 6.25 |
| B. fragilis 0558 | − | 0.05 | 0.10 | 3.13 |
| B. fragilis 25285 | − | 0.05 | 0.10 | 3.13 |
| B. distasonis 8503 | − | 0.39 | 0.39 | 12.5 |
| B. thetaiotaomicron (0661) | − | 0.20 | 0.20 | 25 |
| Fusobacterium necrophorum S-45 | − | − | − | − |
| F. varium KYA 8501 | − | 0.78 | 0.78 | 12.5 |
| Eubacterium lentum GAI 5242 | + | 0.05 | 0.05 | 0.78 |
| Propionibacterium acens 11828 | + | 0.78 | 0.78 | 12.5 |
| Peptococcus magnus KY 017 | + | 0.025 | 0.025 | 0.20 |
| Clostridium difficile I-E | + | 0.39 | 0.39 | 12.5 |
| C. perfringens KYA 13123 | + | 0.10 | 0.10 | 0.39 |
| C. ramosum | + | 0.39 | 0.78 | 6.25 |
| Peptostreptococcus anaerobius KYA 27337 | + | 0.20 | 0.20 | 1.56 |
| Pst. micros UPI 5464-1 | + | 0.05 | 0.05 | 0.78 |
| Veillonella parvula KYA 10790 | − | 0.10 | 0.10 | 0.20 |

CPFX: ciprofloxacin

What is claimed is:

1. A compound of the formula:

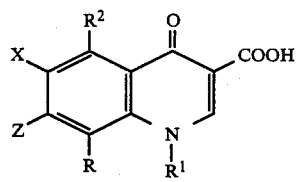

wherein R indicates straight or branched lower alkyl, $R^1$ indicates cycloalkyl having 3 to 6 carbon atoms, straight or branched lower alkyl, halogenalkyl, alkenyl, hydroxyalkyl, lower alkylamino or phenyl, $R^2$ indicates hydrogen, halogen, nitro or amino, X indicates halogen, Z indicates pyrrolidino or piperidino of the following formula:

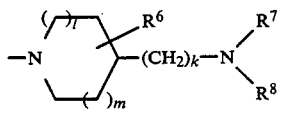

wherein k is 0, 1 or 2, l is 0 or 1 or 2, m is 0 or 1, $R^6$ indicates hydrogen, lower alkyl or hydroxy, $R^7$ indicates hydrogen, lower alkyl, halogenoalkyl or hydroxyalkyl, $R^8$ indicates hydrogen, lower alkyl, lower acyl, alkoxycarbonyl or benzyl; and the hydrates and pharmaceutically acceptable acid addition or alkali salts thereof.

2. The compound defined in claim 1 having the name 7-(3-amino-1-pyrrolidinyl)-1-cyclopropyl-6-fluoro-1,4-dihydro-8-methyl-4-oxo-3-quinolinecarboxylic acid and the pharmaceutically acceptable salts thereof.

3. The compound defined in claim 1 having the name 7-(3-amino-1-pyrrolidinyl)-1-ethyl-6-fluoro-1,4-dihydro-8-methyl-4-oxo-3-quinolinecarboxylic acid and the pharmaceutically acceptable salts thereof.

4. The compound of claim 1, wherein Z is substituted pyrrolidino.

5. The compound of claim 1, wherein Z is substituted piperidino.

6. An antibacterial pharmaceutical composition comprising at least one compound according to claim 1 and an inert pharmaceutically acceptable carrier.

7. The compound defined in claim 1 having the name 7-(3,4-trans-3-amino-4-methyl-1-pyrrolidinyl)-1-cyclopropyl-6-fluoro-1,4-dihydro-8-methyl-4-oxo-3-quinolinecarboxylic acid and the pharmaceutically acceptable salts thereof.

8. The compound defined in claim 1 having the name 7-(3,4-cis-3-amino-4-methyl-1-pyrrolidinyl)-1-cyclopropyl-6-fluoro-1,4-dihydro-8-methyl-4-oxo-3-quinolinecarboxylic acid and the pharmaceutically acceptable salts thereof.

* * * * *